United States Patent [19]

Brinton, Jr.

[11] 4,237,115

[45] Dec. 2, 1980

[54] **METHOD OF IMMUNIZATION AGAINST ENTEROTOXOGENIC INFECTION BY *ESCHERICHIA COLI***

[75] Inventor: Charles C. Brinton, Jr., Pittsburgh, Pa.

[73] Assignee: Bactex, Inc., Pittsburgh, Pa.

[21] Appl. No.: 854,343

[22] Filed: Nov. 23, 1977

[51] Int. Cl.³ ............................................. A61K 39/02
[52] U.S. Cl. ...................................................... 424/92
[58] Field of Search ......................................... 424/92

[56] References Cited

U.S. PATENT DOCUMENTS

| | | | |
|---|---|---|---|
| 3,127,318 | 3/1964 | Eversole et al. | 424/92 |
| 3,975,517 | 8/1976 | Wilson | 424/92 |

OTHER PUBLICATIONS

J. P. Duguid, Revista Latinoamericana de Microbiologia, vol. 7, Suppl. 13/14, Jun.–Dec. 1964, pp. 1–16, Functional Anatomy of *E. coli* with Special Reference to Enteropathogenic *E. coli.*
J. P. Duguid, Archivum Immunologiae et Therapiae Experimentalic, 16, p. 173 (1968), The Function of Bacterial Fimbriae.
G. W. Jones et al., Vet. Bull., 45, No. 11, #6067 (1975), Contribution of the K88 antigen of *E. coli* to enteropathogenicity; protection against disease by neutralizing the adhesive properties of K88 antigen.
G. W. Jones et al., J. Gen'l. Microbiology, 84, 135–144 (1974), The Association of K88 Antigen with Haemagglutinating Activity in Porcine Strains of *E. coli.*
M. Ishibashi, Chemical Abstracts 66: 27352r (1967), F pilus as f⁺antigen.
S. Stirm et al., J. Bacteriology, 93, No. 2, 740–748 (1967), Episome-carried Surface Antigen K88 of *E. coli.*
C. Brinton, Nature, 183, 782–786, (1959), Non-Flagellar Appendages of Bacteria.
E. Stanislavskii et al., Chemical Abstracts, 60: 12534f, (1964), Antigenic properties of the cellular structures of *E. coli.*

*Primary Examiner*—Donald G. Daus
*Assistant Examiner*—M. C. Eakin
*Attorney, Agent, or Firm*—Omri M. Behr

[57] ABSTRACT

There is provided a vaccine material capable of providing a substantial level of protection against infection by enterotoxogenic organisms of *Escherichia coli.* The protecting means comprises pili of the infecting organism. The protection is given either by administering the pili directly to the subject to be protected or to a pregnant female where protection of the newborn is desired. In the case of piglets, where there is substantially no transplacental transfer of immunity from mother to offspring, the pili are administered to mothers, who are then caused to feed the offspring to be protected, whereby the immunization is transferred via the colostrum of the mother.

12 Claims, 1 Drawing Figure

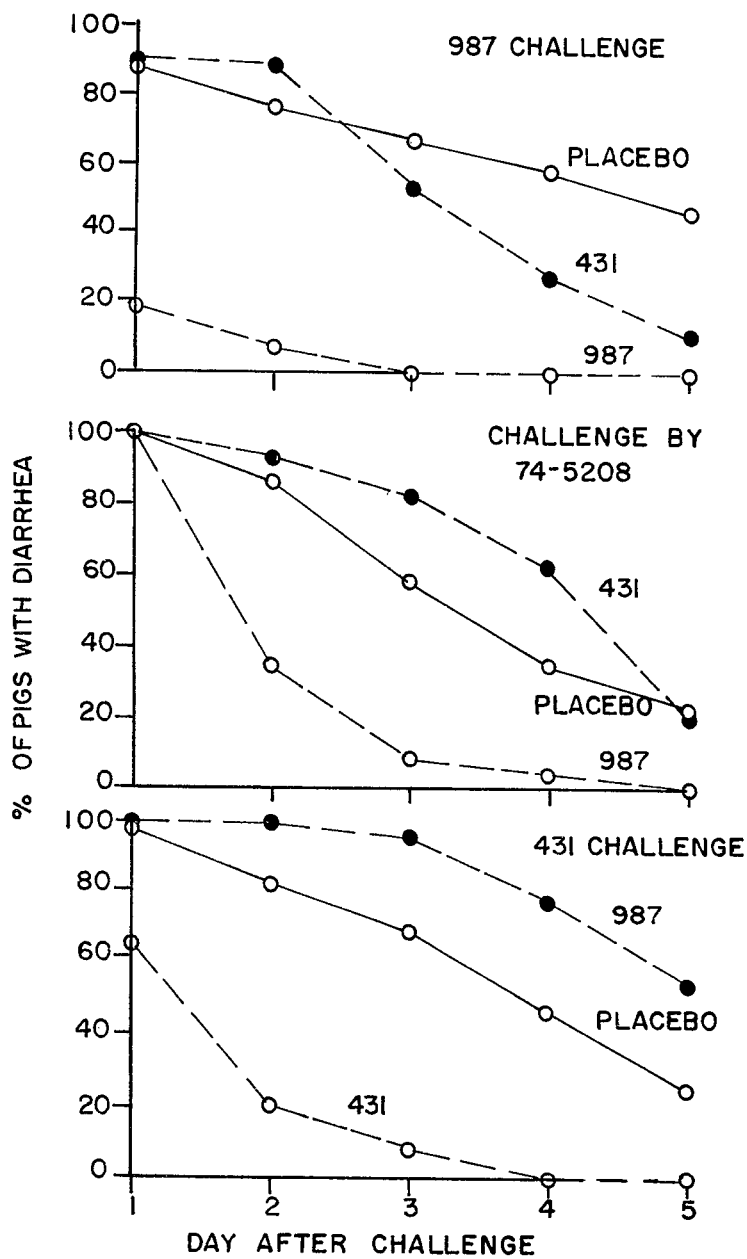

ical composition of the present invention
METHOD OF IMMUNIZATION AGAINST ENTEROTOXOGENIC INFECTION BY *ESCHERICHIA COLI*

BACKGROUND OF THE INVENTION

*Escherichia coli* is a very widespread, often pathogenic, organism which is found in the human as well as domestic animals. The organisms vary in their virulence. While the *E. coli* infection is a widespread problem, it is especially serious in the raising of pigs. It is known that newborn piglets have very low levels of immunity against infection. This level of immunity is extremely low with respect to enterotoxogenic *E. coli*. Under practical pig raising conditions, a substantial number of newborn piglets are infected with enteric colibacillosis which gives rise to acute diarrhea. The effects of this diarrhea, especially the dehydration accompanying it, are of such a level of acuteness that a substantial fraction of the piglets thus infected die during the first six days of life.

Attempts have been made heretofore to isolate immunizing factors and administer same to the piglets. One such approach was taken by Rutter et al (Infection and Immunity 13, 667/676 (1976)) wherein an exocellular factor designated K88 was administered to pre-partum sows whose colostrum was then fed to newborn piglets exposed to virulent *E. coli* infection. In tests carried out on four vaccinated and four unvaccinated litters of between five and eight piglets per litter, the mortality rate of piglets nurtured by vaccinated dams was 12% while that of piglets nurtured by non-vaccinated dams was 68%.

It should be noted that previous studies directed to the nature of the K88 antigens clearly establish that the K88 antigen is not a pilic antigen. Stirm et al (Journal of Bacteriology, 93 740 (1967)).

While these results indicate an improvement over no protection at all, a more effective vaccination procedure and substrate was sought.

SUMMARY OF THE INVENTION

There is provided a vaccine composition capable of raising the antibody level of a vertebrate subject to a level sufficient to provide protection against infection caused by organisms of a first group of strains of piliated *E. coli* comprising:
 (a) Pili derived from a second group of strains of piliated *E. coli* organisms wherein cells of organisms of said first group are agglutinable by serum containing antibodies against pili from said second group, said first group consisting of strains which may be the same or different from the strains of said second group; and,
 (b) a pharmaceutically acceptable carrier.

While there is exemplified in this application a vaccine containing pili from a single pre-determined strain which is effective against infection caused by organisms of the same strain, as well as organisms of a different strain, but same pilic serotype, vaccines which contain pili from several different strains are included within the scope of the present invention provided, of course, that each of said pili will cross-react immunologically with at least one of the infecting organisms.

An important enterotoxogenic strain of *E. coli* was isolated from piglets with diarrhea and shown to be virulent and causative of the natural disease when inoculated into immune-colostrum deprived piglets. This virulent strain, though sparsely piliated, was grown and selected for well-piliated clones. These clones were grown and maintained on blood base agar medium and the pili therefrom separated from the cells and subjected to several cycles of crystallization in aqueous magnesium chloride followed by resolubilization in low ionic strength neutral buffer.

Pregnant dams were injected, pre-partum, with pili. After parturition, piglets were allowed to suckle the immunized dams. Thereafter, the piglets were challenged intragastrically with an amount of *E. coli* previously found to represent one $LD_{50}$ dosage.

No deaths occurred in the immunized group. Although incidence of diarrhea was noted in the immunized group, members of this group recovered rapidly and showed substantial weight/gains over the non-immunized group.

DESCRIPTION OF THE PREFERRED EMBODIMENT

The vaccine compositions of the present invention comprise pili of a pre-determined strain which pili meet certain criteria.

It is known that *E. coli* organisms carry a number of antigenic factors known as "O" antigens (outer membrane) "K" (capsule) and the like, as well as, for certain strains, pili. The criterion of the strain of organisms selected shall be that the strain to be protected against shall be piliated, that the protecting strain shall be piliated, and that the pili of one strain shall give rise to antibodies which cause cells of the other strain to agglutinate in their presence. This simple criterion means that the protecting strains may be homologous or heterologous with respect to the infecting strain as long as the pili of each are immunologically similar. This similarity may, as above, be readily determined by one skilled in the art without undue experimentation.

The pili are selected and obtained by methods well known in the art. One important disease preventable by the methods of the present invention is neonatal porcine colibacillosis. This disease is caused by a gastrointestinal infection of newborn piglets by *E. coli* infection. One infecting strain has been found to be *E. coli* 987.

Culture of *E. coli* 987

Samples of a parental strain *E. coli* 987 (09:K 103:NM) were isolated from piglets suffering from enterotoxogenic *E. coli* infection passed through still broth, and colonial forms selected therefrom, to provide a well pilated clone designated *E. coli* 987-5 (ATCC 31346). The clone is then grown on blood base agar medium. The pili were separated from the cells by blending and centrifugation in a low ionic strength neutral buffer such as 0.01 M MOPS buffer pH 7.5. The pili are crystallized from the buffer by addition thereto of concentrated magnesium chloride (aq) to bring the strength of the buffer up to the 0.10 M whereupon the pili crystallize. The crystalline pili are taken up in a low ionic strength neutral buffer such as 0.01 M MOPS buffer pH 7.5 and reprecipitated with magnesium chloride in a similar manner. It is preferred to subject the pili to from one to five cycles of recrystallization. The procedure used is that substantially set forth in Brinton, *Trans. N. Y. Acad. Sci* 27, 1003 (1965).

The final preparation of the pilus vaccine consists of dialyzing the recrystallized pili against saline, suitably saline containing formaldehyde, most suitably containing between 0.1 and 0.7 M formaldehyde. The pili thus prepared are of a quality sufficient to pass the standards of the Bureau of Biologics, Food and Drug Administration, for general safety, sterility, and pyrogenicity.

The pili may be administered orally—say, in capsule form—or by injection—that is to say, subcutaneous, intradermal, or intramuscular injections. Where the mode of administration is by injection, since the pili are solid, any pharmaceutically acceptable suspending medium may be employed. It has been found especially useful to employ saline, suitably containing formaldehyde, as the vehicle or suspending medium. It is preferred to use 0.7-0.9, most suitably 0.85%, saline containing 0.01 to 0.1, most suitably 0.05%, formaldehyde. The concentration of pili in the vehicle is not critical. The sole criterion of desirability being that the pili shall be sufficiently finely divided to provide a suspension which meets generally accepted standards of syringeability. A concentration of 0.1-1, preferably about 0.5 mg of pilus protein per ml of suspending medium is especially suitable.

It is generally preferred to administer the vaccine composition in more than one dose separated by a predetermined time factor. This time factor is selected to permit the formation of an adequate titer of antibodies to the pili in the injected subject. In the case of pregnant sows, it has been found suitable to administer the vaccine composition at least once between 5 and 30 days pre-partum (farrowing). It has been found most suitable to inject the sow subcutaneously with a first injection 27 to 21 days before farrowing and a second injection 13 to 7 days before farrowing.

Since there are no local or systemic toxic effects engendered by the injection of vaccine, there appear to be no upper limits to the dosage administered. It has been found suitable, however, to administer between 1 and 100 micrograms of pili per kilogram of body weight, most suitably about 60 micrograms per kilogram of body weight in each injection.

After farrowing, the piglets are set to suckle an immunized dam. While, in the normal course of events, it would be expected that a newborn piglet would be suckled by its own dam and thereby ingesting colostrum or milk containing the pre-partum generated antibodies to the E. coli, the mode of administration of the colostrum to the piglets is not limited thereto. The colostrum can be fed to the piglets by any suitable means including the direct oral administration—for example, by bottle feeding. It should also be noted that the piglets may be suckled by any previously immunized dam, such dam need not necessarily have been the piglet's own dam. The normal amount of colostrum ingested by a newborn piglet at its first suckling will generally be sufficient to provide the piglet with enough immunization to reduce the severity of any E. coli infection which it may acquire to a level from which an otherwise healthy piglet will recover from within one to six days. Needless to say, continued suckling for longer periods will increase the level of protection and thus reduce the likelihood of any E. coli infection appearing in the piglet.

In further challenge experiments, the challenge was made with another E. coli strain which, in cell agglutination tests, agglutinates in serum containing antibodies to E. coli 987-5 (ATCC 31346). This challenge strain, designated E. coli 74-5208 (ATCC 31347), has different "O" and "K" antigens. The degree of protection against this strain was not quite as great as against homologous (i.e., 987-5) challenge. Nevertheless, the thus challenged piglets had a substantially higher resistance level and survival rate than the piglets from unvaccinated dams.

It should be noted that, while the immunization of a newborn piglet by the feeding of colostrum from previously immunized pregnant dams is the especially preferred embodiment of the present invention, the invention is by no means limited thereto.

E. coli infection occurs, due to many different strains thereof, in different species of mammals. It has been found that E. coli species having Type I pili are responsible for human infections. Thus, the pili derived from related members of said group of species will provide protecting antibodies in a system into which they are administered.

EXAMPLE I

Preparation of Escherichia Coli Pili

E. coli somatic pili from pre-determined strains (74-5208 (ATCC 31347) and 987-5 (ATTC 31346)) were purified by crystallization with magnesium ion and solubilization of the crystals in its absence.

A culture prepared by resuspending piliated phase colonies growing on blood agar base medium in a liquid glucose-yeast extract-tryptone medium was used to inoculate trays containing the same gross medium solidified with agar. After overnight incubation at 37° C., the confluent bacterial grown was suspended in 0.05 molar MOPS (morpholinopropanesulfonic acid) buffered saline (0.85%) pH 7.2. About twenty milliters of buffer was used to suspend the growth from one tray which dimensions were approximately 30 cm×40 cm. The resuspended growth was blended, 200 milliliters at a time, at 14,000 rpm for five minutes in the 400 milliliter cup of a Sorvall ® OMNIMIXER in order to remove pili from the cells. Cells were then removed by centrifugation at 10,000 times G for twenty minutes and the supernatant liquid was retained. The pili were then crystallized by the addition of magnesium chloride (MgCl$_2$) to 0.1 molar. After the crystals formed, they were removed from suspension by centrifugation at 20,000 times G for sixty minutes, and the pellet was retained. The pellet containing the pilus crystals was redissolved in 0.01 molar MOPS buffer pH 7.2 (without saline). The suspension was clarified by centrifugation at 20,000 times G for sixty minutes and the supernatant liquid was retained. The cycle of crystallization, centrifugation, redissolution, and centrifugation was repeated two to four times to obtain the purified pilus suspension.

The strains of E. coli, 74-5208 and 987-5 have been deposited under ATCC numbers 31346 and 31347 respectively in the American type Culture Collection 12301 Parklawn Drive, Rockville, Md. 20852.

EXAMPLE II

Mode of Immunization

The vaccine and the mode of protecting newborn piglets was evaluated with a group of 17 pregnant sows. Nine sows were injected with pili and eight with vehicle. The vehicle utilized saline (0.85%) and formaldehyde (0.05%). The vaccine consisted of vehicle containing 0.5 mg of pili per ml of vehicle. E. coli 987-5 (ATCC 31346) and 74-5208 (ATCC 31347) pili were used. Each vaccinated sow received approximately 9 mg of pili per sow or a dosage circa 60 micrograms per kilogram. Injections were given subcutaneously in the flank at between 21 and 27 days and again 7 through 13 days before farrowing. No local or systemic toxic effects were noted. Blood samples were taken from all sows immediately before farrowing and 100 to 200 ml of colostrum drawn manually from each sow during parturition. These samples were used for the antibody tests set forth below. After parturition, the piglets were allowed to suckle their dams for 30 minutes before challenge.

EXAMPLE III

Preparation of Inocula for *E. coli* 987 and 74-5208

Inocula. A colony of heavily piliated 987 bacteria was picked from pure culture on blood agar plates and was inoculated into 10 ml starter cultures of Trypticase soy broth (TCSB). After incubating at 37° C. without shaking for 16 hours, 1 ml of starter culture was used to inoculate 1 liter Erlenmeyer flasks containing 500 ml TCSB. With 74-5208, the flasks were inoculated directly with small, translucent colonies of heavily piliated 74-5208 bacteria selected from pure cultures on sheep blood agar. After incubating the flasks at 37° C. for 18 to 22 hours without shaking, the bacteria were harvested by centrifugation at 7,000 times G for ten minutes. The pelleted bacteria were resuspended in half strength TCSB containing 10% glycerol at 10 times the challenge concentration. The two inocula were stored at $-70°$ C. for up to seven months in aliquots containing enough inoculum for each litter.

EXAMPLE IV

Homologous Challenge (987 v. 987)

At birth, pigs were separated from the gilts for 2–6 hours, until all were born. They were then weighed and returned to the gilts for 30 minutes and allowed to suckle. After this initial colostrum intake, each pig was inoculated intragastrically with strain 987. The stock inoculum was kept frozen at $-70°$ C., in 10% glycerol and contained $5.4 \times 10^8$ viable bacteria per ml. Immediately before the inoculation of each litter, one vial containing 1 ml of the frozen inocula was thawed out and 0.25 ml of it was diluted in 15 ml of cold trypicase soy broth (TCSB). One ml of this TCSB dilution, containing about $9 \times 10^6$ viable bacteria, was added to an additional 10 ml of cold TCSB and inoculated into each pig intragastrically via stomach tube. This dose was chosen because preliminary experiments indicated it was an approximate $LD_{50}$.

Results of Homologous Challenge

The vaccinated and non-vaccinated piglets were subjected to certain tests which are summarized in Table I below. The tests are as follows:
1. Intestinal colonization
2. Adhesion of bacteria to the ilial epithelium
3. Death
4. Diarrhea
5. Weight gain

TABLE I

VACCINE EXPERIMENT I
Response of pigs, nursing vaccinated[a] and nonvaccinated gilts to challenge with enterotoxigenic *E. coli* 987

| Group | Dam No. | 16 h after challenge | | 6 days after challenge Survivors | | |
|---|---|---|---|---|---|---|
| | | $Log_{10}$ *E. coli*/ 10 cm ileum | Association index | Death/ total | Diarrhea/ total | Weight gain gram/h |
| Vaccinated | 1 | 8.6 | 1.0 | 0/8 | 0/8 | 7.8 |
| | 2 | 8.1 | 1.7 | 0/7 | 0/7 | 8.9 |
| | 5 | 8.4 | 1.0 | 0/11 | 0/11 | 8.6 |
| | 6 | 8.9 | 1.0 | 0/8 | 0/8 | 6.5 |
| | 10 | 6.0 | 1.0 | 0/11 | 0/11 | 4.5 |
| | 11 | 7.9 | 1.0 | 0/6 | 0/6 | 5.0 |
| | 12 | 6.0 | 1.0 | 0/3 | 0/3 | 4.4 |
| | 15 | 6.0 | 2.5 | 0/7 | 0/7 | 7.2 |
| | 16 | 6.0 | 2.0 | 0/8 | 0/8 | 7.3 |
| | | $\overline{X}=7.3^b$ | $\overline{X}=1.2$ | $\Sigma=0/69^c$ | $\Sigma=0/69$ | $\overline{X}=6.7$ |
| Nonvaccinated | 3 | 8.7 | 1.0 | 0/7 | 0/7 | 8.8 |
| | 4 | 10.2 | 5.0 | 7/10 | 3/3 | 1.3 |
| | 7 | 9.8 | 1.0 | 1/6 | 3/5 | 6.3 |
| | 8 | 8.9 | 4.2 | 6/11 | 1/5 | 1.3 |
| | 9 | 10.8 | 5.0 | 1/3 | 2/2 | 0.3 |
| | 13 | 10.4 | 4.2 | 2/8 | 0/6 | 1.2 |
| | 14 | 8.2 | 1.0 | 0/7 | 2/7 | 5.8 |
| | 17 | 6.0 | 1.0 | 0/4 | 0/4 | 8.9 |
| | | 9.1 | 2.8 | 17/56 | 11/39 | 4.2 |
| t test | | P < .05 | P < .05 | P < .001 | P < .001 | P < .05 |

[a]Vaccinated with purified pili of *E. coli* strain 987;
[b]Mean;
[c]Total.

DISCUSSION OF RESULTS

1. Intestinal colonization

Sixteen hours after challenge, one piglet, selected as the weakest, from each litter was killed. Sections of the ileum of all test animals were removed and examined for the presence of *E. coli* bacteria. The results show that the piglets suckled by the non-immunized dams had viable bacteria of approximately two orders of magnitude more per 10 cm section of ileum than the piglets suckled by the vaccinated dams. It was also noted that the former group (three animals tested) showed richly piliated colonies of *E. coli* 987 while no such colonies were found in a similar number of test animals in the latter group.

2. Association Index

This test measured the degree of adhesion of the challenge strain to the ileal epithelium. Ileal sections were stained with antibody to *E. coli* 987 coupled with fluorescein. This material, when adhered to a substrate, will fluoresce in uv light.

The degree of adhesion is expressed on a scale of 0 through 5. The difference in association index of 1.6 units between the vaccinated and non-vaccinated test animals is statistically significant (p is less than 0.05).

3. Death

No deaths occurred in the vaccinated group. Approximately 30% of the non-immunized group died of colibacillosis during the first six days of life, most deaths occurring on the second and third days.

4. Diarrhea

It should be noted that the Table refers to surviving test animals showing symptoms of diarrhea six days after challenge. In observations made 16 hours after challenge, 56% of the immunized group had diarrhea, while 72% of the non-immunized had diarrhea. Nevertheless, it should be noted from the Table that the immunized group recovered rapidly, while six days after challenge 28% surviving non-immunized pigs still had diarrhea.

5. Weight gain termine the in vivo immune relationship between two strains of the same pilus type—i.e. 987 (serotype 09:K103, 987-P:NM) and 74-5208 (serotype 0.20:K 101, 987-P:NM), and a third strain, having an exocellular proteinaceous appendage of a different K serotype—i.e, 431 (serotype 0101:K30, K99:NM). Pregnant sows were inoculated with placebo and pili from the piliated strains and the appendage protein from the third strain. The piglets were suckled to post-partum sows, and randomly selected piglets challenged with each of the foregoing strains.

The results show homologous and heterologous protection between 987-5 and 74-5208 and homologous protection between 431 challenge and 431 appendage protein, but not between the two groups. These results are summarized in the FIGURE which shows percentage of remaining pigs with diarrhea verses day after challenge for each vaccine-challenge strain group.

The serological (antigen/antigen) relationship is summarized in Table II below.

TABLE II

SERUM AND COLOSTRUM ANTIBODY TITERS IN NON-IMMUNIZED,
987-5 PILUS IMMUNIZED AND 431 IMMUNIZED PREGNANT SOWS

Cell agglutination titers. Two-fold serum dilution series. One assay. Geometric mean of 6 sows in each group

| Immunization | cells used for assay | 1st bleeding (pre-immunizing) | 2nd bleeding | 3rd bleeding | Colostral whey |
|---|---|---|---|---|---|
| None (Saline-Formaldehyde) | 987-5 | 3.0 | 4.0 | 4.6 | 3.2 |
|  | 74-5208 (987 pili) | 3.0 | 3.0 | 2.6 | 4.0 |
|  | 431 | 18.4 | 12.1 | 12.1 | 10.6 |
| 987-5 purified pili in saline-formaldehyde | 987-5 | 3.5 | 128.0 | 388.0 | 2,352.5 |
|  | 74-5208 (987 pili) | 7.0 | 512.0 | 1024.0 | 2,352.5 |
|  | 431 | 16.0 | 10.6 | 36.8 | 73.5 |
| 431 purified antigen* saline-formaldehyde (protein-appendage) | 987-5 | 3.5 | 4.5 | 5.0 | 8.0 |
|  | (987 pili) | 3.5 | 5.7 | 3.6 | 6.1 |
|  | 431 | 16.0 | 322.5 | 456.1 | >4,096 |

The rate of weight gain in grams per hour was substantially greater among the immunized piglets than the non-immunized piglets—significance here again being p is less than 0.05 (using the t test).

EXAMPLE V

Heterologous Challenge

Substantially in accordance with the foregoing challenge procedures, experiments were carried out to de- A similar comparison to that of Table II above was performed which showed that the administration of pili to pregnant sows had no effect on the serum level of the "O" antigen, one of the other E. coli antigens. The results are set forth in Table III below.

The results of this "O" antigen experiment support the position that the pili are responsible for the immunity conferred against challenge by piliated organisms of similar pilus serotype.

TABLE III

VACCINE EXPERIMENT I
MEANS AND RANGES OF GROUPED E. COLI 987 0 ANTIGEN TUBE
AGGLUTINATION TITERS OF SOW SERA AND COLOSTRAL WHEY

| Body Fluid Assayed | Statistic | Pre-immune and/or Non-immune | Post-immune | Ratio of Post-immune to Pre-immune |
|---|---|---|---|---|
| Serum | Geometric Mean* | 44 | 69 | 1.6 |
|  | Range | 26–72 | 33–148 | 1.0–2.6 |
|  | Log Mean ± 2 S$\bar{x}$ | 1.64 ± 0.22 | 1.84 ± 0.33 | 0.20 ± 0.21 |
| Colostral Whey | Geometric Mean* | 191 | 219 | 1.1 |
|  | Range | 91–398 | 145–331 | 0.7–1.8 |

TABLE III-continued

VACCINE EXPERIMENT I
MEANS AND RANGES OF GROUPED E. COLI 987 0 ANTIGEN TUBE
AGGLUTINATION TITERS OF SOW SERA AND COLOSTRAL WHEY

| Body Fluid Assayed | Statistic | Pre-immune and/or Non-immune | Post-immune | Ratio of Post-immune to Pre-immune |
|---|---|---|---|---|
| | Log Mean ± 2 S$\bar{x}$ | 2.28 ± 0.32 | 2.34 ± 0.18 | 0.06 ± 0.20** |

*In calculating the geometric mean a titer of less than 10, the lowest dilution used, is taken to be 5.
** ± Value is twice the standard error of the difference of the means of the logs of titers computed from the formula $$\sigma_{\bar{x}_1-\bar{x}_2} = \sqrt{\frac{S_1^2}{N_1-1} + \frac{S_2^2}{N_2-1}} \quad ().$$

I claim:

1. A vaccine composition capable of raising the antibody level of pigs to a level sufficient to provide protection against neonatal porcine colibacillosis caused by a member of a first group of strains of piliated E. coli, comprising
   (a) pili previously separated from other E. coli organism components derived from at least one member of a second group of strains of piliated E. coli organisms wherein cells of organisms of said first group are agglutinable by serum containing antibodies against pili from said second group, said first group consisting of strains which may be the same as or different from the strains of said second group, and
   (b) a pharmaceutically acceptable carrier.

2. A vaccine of claim 1 comprising pili derived from more than one member of the second group of strains wherein each of said members of said second group are capable of producing antibodies which will cause the cells of at least one member of said first group to agglutinate in their presence.

3. A composition of claim 1 wherein a strain of the second group is E. coli 987-5 (ATCC 31346) or 74-5208 (ATCC 31347).

4. A composition of claim 3 comprising 1–10 mg of pili of the second group per 10 ml of injectable vehicle.

5. A composition of claim 4 wherein the vehicle is physiologically acceptable saline.

6. A method of protecting newborn piglets against neonatal porcine colibacillosis caused by a member of a predetermined first group of strains of piliated E. coli which comprises (a) administering pre-partum to pregnant sows a composition comprising pili derived from at least one member of a second group of strains of piliated E. coli organisms wherein cells of organisms of said first group are agglutinable by serum containing antibodies against pili from said strains which may be the same as or different from strains of said second group; said first group consisting of strains which may be the same as or different from the strains of said second group;
   (b) administering colostrum or milk derived postpartum from the aforesaid sows to newborn piglets.

7. A method of claim 6 wherein the vaccine composition is administered at least once to the pregnant sows between about 5 and about 30 days pre-partum.

8. A method of claim 7 wherein there is administered between 1 and 100 µg/Kg body weight of the pilic component of vaccine composition.

9. A method of claim 7 wherein the pilic component of the vaccine composition is derived from pili of E. coli 987-5 (ATCC 31346) or E. coli 74-5280 (ATCC 31347).

10. A method of claim 6 wherein the colostrum is administered by suckling the newborn piglets to previously vaccinated post-partum sows.

11. A method of claim 6 wherein the colostrum is drawn from post-partum sows and fed to newborn piglets.

12. A vaccine of claim 1 comprising pili derived from more than one member of the second group of strains wherein each of said members of said second group are capable of producing antibodies which will cause the cells of at least one member of said first group to agglutinate in their presence.

* * * * *

UNITED STATES PATENT AND TRADEMARK OFFICE
CERTIFICATE OF CORRECTION

PATENT NO. : 4,237,115
DATED : December 2, 1980
INVENTOR(S) : Charles C. Brinton, Jr.

It is certified that error appears in the above-identified patent and that said Letters Patent are hereby corrected as shown below:

Insert into claim 6 at column 10, line 2, after "pili" the words "separated from other E. coli organism components"

Signed and Sealed this

Sixth Day of September 1983

[SEAL]

Attest:

GERALD J. MOSSINGHOFF

Attesting Officer     Commissioner of Patents and Trademarks